United States Patent
Müller et al.

(10) Patent No.: US 12,178,480 B2
(45) Date of Patent: Dec. 31, 2024

(54) SYSTEM AND METHOD FOR ESTABLISHING AN ANCHORAGE OR REINFORCEMENT IN AN OBJECT WITH THE AID OF IN SITU LIQUEFACTION AND DISPLACEMENT OF A MATERIAL HAVING THERMOPLASTIC PROPERTIES

(71) Applicant: Woodwelding AG, Stansstad (CH)

(72) Inventors: Andrea Müller, Winterthur (CH); Andrè Schwery, Rombach (CH); Philipp Bernhard, Thun (CH); Mario Weiss, Diessbach bei Büren (CH)

(73) Assignee: WOODWELDING AG, Stansstad (CH)

( * ) Notice: Subject to any disclaimer, the term of this patent is extended or adjusted under 35 U.S.C. 154(b) by 1100 days.

(21) Appl. No.: 16/967,879

(22) PCT Filed: Feb. 6, 2019

(86) PCT No.: PCT/EP2019/052870
§ 371 (c)(1),
(2) Date: Aug. 6, 2020

(87) PCT Pub. No.: WO2019/154835
PCT Pub. Date: Aug. 15, 2019

(65) Prior Publication Data
US 2021/0045786 A1  Feb. 18, 2021

(30) Foreign Application Priority Data
Feb. 8, 2018  (CH) .................................... 00149/18

(51) Int. Cl.
*A61B 17/70* (2006.01)
*A61B 17/56* (2006.01)
(Continued)

(52) U.S. Cl.
CPC ...... *A61B 17/7098* (2013.01); *A61B 17/7032* (2013.01); *A61B 17/7035* (2013.01);
(Continued)

(58) Field of Classification Search
CPC ...... A61B 17/86–95; A61B 17/68–688; A61B 17/88–8897
See application file for complete search history.

(56) References Cited

U.S. PATENT DOCUMENTS 5,167,619 A * 12/1992 Wuchinich ....... A61B 17/32002
606/171
6,921,264 B2  7/2005 Mayer et al.
(Continued)

FOREIGN PATENT DOCUMENTS

DE  43 16 543  7/1994
WO  2009/010234  1/2009
(Continued)

*Primary Examiner* — Matthew J Lawson
(74) *Attorney, Agent, or Firm* — Rankin, Hill & Clark LLP

(57) ABSTRACT

A system for establishing an anchorage or augmentation in hard tissue with the aid of a material having thermoplastic properties, which is brought to the site of the anchorage or reinforcement in a solid state, is liquefied in situ, and, in a liquefied state, is displaced to contact the object. The system includes a housing with a proximal housing part and mounted therein, a transmitting piece possibly coupled to an energy source and a driver spring, a distal housing part releasably coupled to the proximal housing part, a permeable sleeve couplable to the distal housing part, and a thermoplastic element positionable in the permeable sleeve. The two housing parts, the transmitting piece, the driver spring and the permeable sleeve form a closed load frame in which the thermoplastic element is compressed between the transmitting piece and the permeable sleeve.

14 Claims, 9 Drawing Sheets

(51) Int. Cl.
*A61B 17/86* (2006.01)
*A61B 17/88* (2006.01)
*B29C 65/00* (2006.01)
*B29C 65/08* (2006.01)
*F16B 37/08* (2006.01)
*A61B 17/00* (2006.01)

(52) U.S. Cl.
CPC ...... *A61B 17/7082* (2013.01); *A61B 17/8836* (2013.01); *B29C 65/08* (2013.01); *B29C 66/30325* (2013.01); *B29C 66/532* (2013.01); *B29C 66/534* (2013.01); *B29C 66/7392* (2013.01); *B29C 66/8161* (2013.01); *B29C 66/8322* (2013.01); *F16B 37/0892* (2013.01); *A61B 2017/00955* (2013.01); *A61B 2017/564* (2013.01); *A61B 2017/8655* (2013.01)

(56) References Cited

U.S. PATENT DOCUMENTS

| | | | | |
|---|---|---|---|---|
| 7,335,205 | B2* | 2/2008 | Aeschlimann | B29C 66/21 |
| | | | | 606/232 |
| 9,421,005 | B2* | 8/2016 | Bonutti | A61B 17/686 |
| 2008/0109007 | A1* | 5/2008 | Schwager | A61B 17/92 |
| | | | | 606/104 |
| 2009/0018471 | A1* | 1/2009 | Dorawa | A61B 17/7098 |
| | | | | 606/86 R |
| 2010/0256688 | A1* | 10/2010 | Giersch | A61B 17/864 |
| | | | | 606/301 |
| 2011/0046670 | A1* | 2/2011 | Lehmann | A61B 17/0401 |
| | | | | 606/232 |
| 2011/0118744 | A1* | 5/2011 | Lehmann | A61B 17/00491 |
| | | | | 606/104 |
| 2011/0251600 | A1* | 10/2011 | Giersch | A61B 17/864 |
| | | | | 606/2 |
| 2012/0041447 | A1 | 2/2012 | Schwer et al. | |
| 2012/0143261 | A1* | 6/2012 | Giersch | A61B 17/864 |
| | | | | 606/304 |
| 2013/0103039 | A1 | 4/2013 | Hopkins et al. | |
| 2014/0114362 | A1* | 4/2014 | Giersch | A61B 17/864 |
| | | | | 606/104 |
| 2016/0296266 | A1* | 10/2016 | Chandanson | B25B 23/0035 |
| 2018/0250033 | A1* | 9/2018 | Müller | A61B 17/68 |
| 2018/0368893 | A1* | 12/2018 | DiVincenzo | A61B 17/7082 |

FOREIGN PATENT DOCUMENTS

| | | |
|---|---|---|
| WO | 2009/010247 | 1/2009 |
| WO | 2009/055952 | 5/2009 |
| WO | 2010/045751 | 4/2010 |
| WO | 2010/127462 | 11/2010 |
| WO | 2011/054123 | 5/2011 |
| WO | 2011/091545 | 8/2011 |
| WO | 2017/054099 | 4/2017 |

* cited by examiner

State of the art

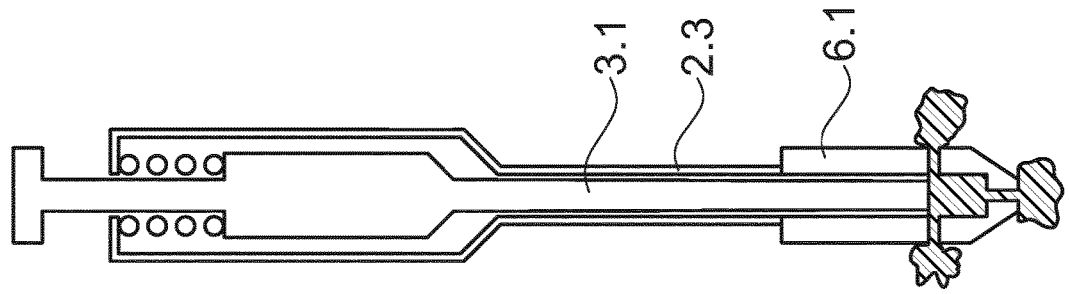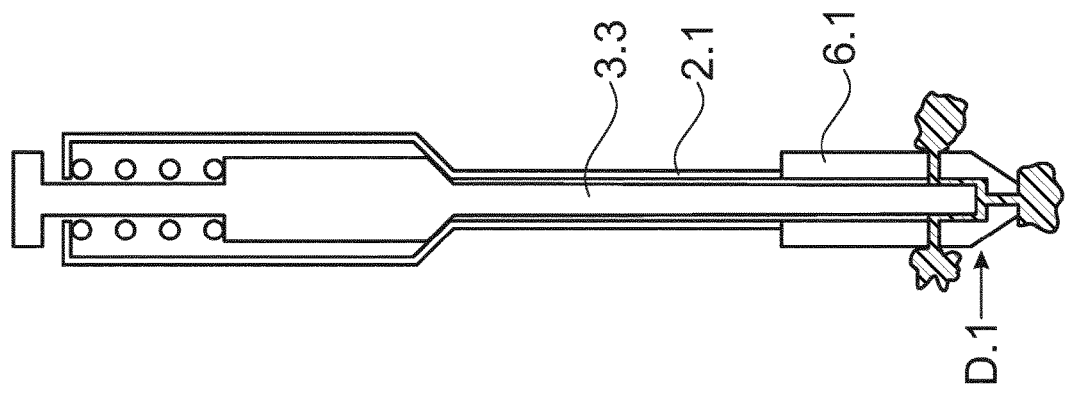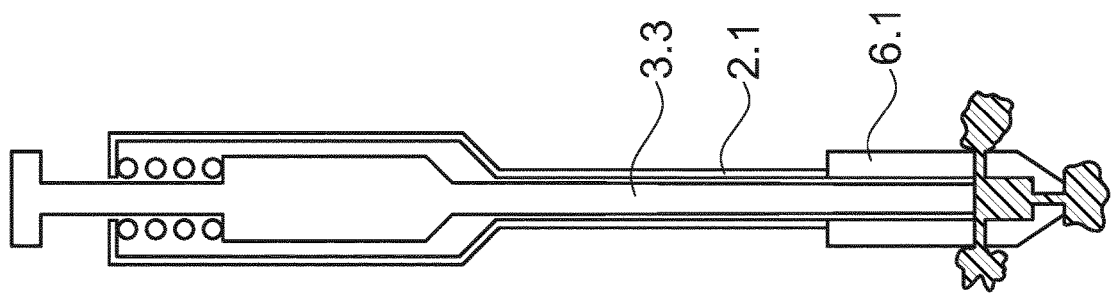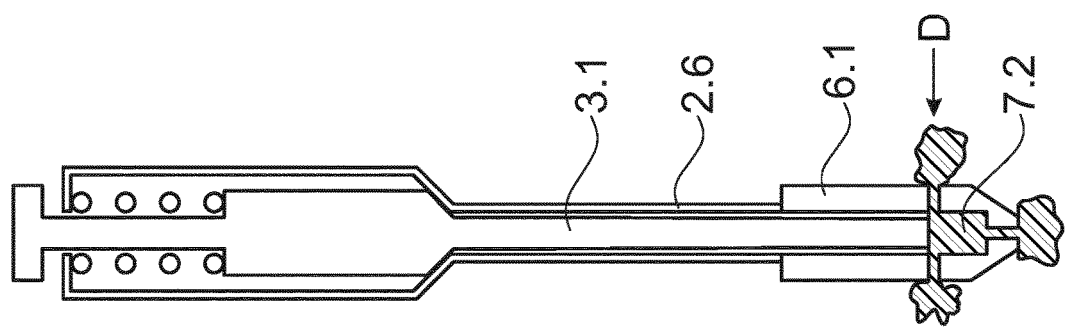

SYSTEM AND METHOD FOR ESTABLISHING AN ANCHORAGE OR REINFORCEMENT IN AN OBJECT WITH THE AID OF IN SITU LIQUEFACTION AND DISPLACEMENT OF A MATERIAL HAVING THERMOPLASTIC PROPERTIES

BACKGROUND OF THE INVENTION

Field of the Invention

The invention relates to a system and a method for establishing an anchorage or a reinforcement in an object with the aid of in situ liquefaction and displacement of a material having thermoplastic properties. The system and method are in particular applicable in the medical field of minimally invasive or open surgery, wherein the object, in which the anchorage or the reinforcement (augmentation) is to be established, is in particular a hard tissue object (e.g., a bone) or includes hard tissue replacement material. The system and the method are also applicable in many non-medical technical fields, in which case the object consist in particular of a porous or fibrous material (e.g., wood or chip-board) or of a foam material (e.g., metal foam), but may consist also of another, denser material including suitable surfaces or structures (e.g., rough surface or surface with undercut cavities), at least where the anchorage or reinforcement is to be established.

In the following, the invention is described in mainly medical terms, but this fact is not to be construed as a limitation of the invention to the medical field.

Description of Related Art

In the whole of the present description, the terms "distal" and "proximal" are used for designating opposite sides or ends of the main parts of the system, wherein a "longitudinal axis" of the parts extends between the distal and the proximal part ends. Therein, in an assembled configuration of the system, the longitudinal axes of the system parts are coinciding with or parallel to each other, and in many cases coinciding with or parallel to an implantation direction. The term "longitudinal axis" and the corresponding term "axial length" for an extension in the direction of the longitudinal axis do not necessarily mean that a system part (in particular the permeable sleeve and the thermoplastic element) necessarily has its greatest extension along its longitudinal axis, or that the axial length of the part is necessarily its greatest extension respectively. The terms "in a proximal direction" or "in a distal direction" are to mean towards a more proximal position or towards a more distal position relative to another system part.

A known method for establishing an anchorage or augmentation (local reinforcement) in hard tissue or hard tissue replacement material forming the basis of the present invention uses a cannulated sleeve with an open proximal end, with an at least partly closed distal end, and possibly with penetrable lateral walls (e.g., lateral fenestration, walls with open porosity, or other suitable structures) connecting the central opening (cannulation) of the sleeve with lateral sleeve surfaces. In the following, the correspondingly equipped sleeve is referred to as "permeable sleeve". An initially solid element including the material having thermoplastic properties (in the following referred to as "thermoplastic element") is positioned in the central opening of the permeable sleeve and the sleeve is positioned relative to the hard tissue or replacement material, in most cases in an opening in the hard tissue or hard tissue replacement material. Using suitable tooling, the thermoplastic element is pushed against the at least partly closed distal sleeve end and energy is applied to the thermoplastic element such that the material having thermoplastic properties is at least partly liquefied, and, in a liquefied state, is pressed out of the permeable sleeve (displaced). The such displaced material fills spaces between the sleeve and the hard tissue surrounding the latter or it fills cavities in the wall of the opening in the hard tissue, and/or it penetrates the structure of the wall of the opening, and, on re-solidification, constitutes a positive fit connection with the hard tissue and/or a sort of composite with the hard tissue. After completion of the anchoring or reinforcement, the permeable sleeve usually remains in the hard tissue whilst the rest of the system is removed.

Known systems for carrying out the above briefly described anchoring or reinforcing process comprise, in addition to the permeable sleeve and the thermoplastic element, an instrument, e.g., in the form of a hand piece suitable for manual operation, which instrument is capable firstly of pressing the thermoplastic element into the sleeve and secondly of transmitting the energy necessary for the liquefaction to the thermoplastic element. The named energy is in particular ultrasonic vibration energy supplied by an ultrasonic transducer unit which is preferably integrated in the hand piece, the vibration energy is transmitted to the thermoplastic element via a sonotrode (transmitting piece) coupled to the transducer unit, while the distal face of the sonotrode is pressed against the thermoplastic element, either manually or by a suitable drive integrated in the instrument.

The publication WO2011/054123 discloses a system which is suitable for carrying out the above briefly described method. The instrument of the disclosed system is a hand piece and includes a housing in which the transducer unit and, coupled thereto, the sonotrode, and a driver spring are arranged, such that the combination of transducer unit and sonotrode is axially moveable within the housing in a limited manner and is acoustically decoupled from the housing, such that a distal end of the sonotrode is able to protrude from a distal housing end, and such that the driver spring, acting between a proximal housing portion and the transducer unit, biases the combination of transducer unit and sonotrode away from the proximal end of the housing. In an assembled configuration of the system, in which the permeable sleeve with the thermoplastic element positioned therein is coupled to the distal end of the housing, the system parts form a closed load frame in which the thermoplastic element is compressed between the distal face of the sonotrode and the permeable sleeve and the coupling between the housing and the permeable sleeve transmits the tensile force (re-action of compression force acting on the thermoplastic element). On activation of the transducer unit and release of the driver spring from a locked initial position, the material having thermoplastic properties of the thermoplastic element is at least partly liquefied and displaced through the permeable sleeve by the action of the driver spring which maintains the compression force and compensates the proximodistal shortening of the thermoplastic element through displacement of the liquefied material.

The permeable sleeve according to WO2011/054123 is in particular a bone screw, e.g., a pedicle screw, which is augmented in the above described manner after being screwed into the hard tissue. For coupling the screw to the instrument, or the housing thereof respectively, a distal portion of the housing includes on its inside a secondary cannulated shaft being rotatable relative to the housing and carrying, on its distal end, an outer thread being adapted to an inner thread in the screw head. Furthermore, the distal housing end is equipped for a non-rotatable push-on connection with the screw. Coupling of the housing to the screw is achieved by pushing the housing against the screw head for push-connecting it with the screw and then rotating the rotatable secondary shaft relative to the housing for engaging the two threads with each other. For rendering the system suitable for minimally invasive surgery, the distal portion of the housing has a smaller cross section than the rest of the housing and has an axial length in the region of 100 mm.

A less automated system serving a similar purpose as the system according to WO2011/054123 is described in the publication WO2011/091545. The system according to WO2011/091545 does not include a drive nor means for coupling the instrument to the permeable sleeve. This means that, for the liquefaction process, the instrument needs to be e.g., manually pressed against the permeable sleeve, wherein the compression force is counteracted by the hard tissue in which the permeable sleeve is positioned or by a preliminary anchorage (e.g., screw connection) of the sleeve in the hard tissue. For simplifying the method and for making it more suitable for minimally invasive surgery, WO2011/091545 proposes to couple the permeable sleeve initially to a cannulated applicator piece, wherein the applicator piece is used, on the one hand, for positioning the permeable sleeve in the hard tissue prior to the liquefaction step, and, on the other hand, as a guide tube for introducing the distal portion of the sonotrode into the permeable sleeve positioned in the hard tissue in preparation of the liquefaction process. The proposed applicator piece has the form of a double cannulated shaft and its distal end is equipped in a similar manner as the distal housing portion according to WO2011/054123.

A further known system similar to the system according to WO2011/054123 is described in the publication WO 2009/010234. This system again constitutes in an assembled configuration a closed load frame in which the thermoplastic element is compressed between the transmitting piece and the permeable sleeve, the compression force being counteracted by a tensile force being transmitted from the permeable sleeve to the housing through a suitably tensile loadable coupling between the permeable sleeve and the housing. The housing of the system according to WO 2009/010234 includes a proximal cap, which is coupled to the rest of the housing with the aid of a pair of cooperating threads or with the aid of a plurality of circumferential grooves, and balls biased into a selected one of the grooves such that the axial length of the housing is continuously or incrementally adjustable. According to the teaching of WO 2009/010234, this adjustability is primarily used for adjusting the compression force exercised by the driver spring and possibly, combined therewith, also for adapting the system to differing lengths of permeable sleeves to be used together with the instrument. A similar system is disclosed in the publication US2011/0251600, which system is equipped for adaptation to differing lengths of permeable sleeves through adaptation of an overall axial length of the housing by including two housing parts being screwable into each other, wherein the adaptation has no effect on the compression force.

Publication WO2017/054099 discloses a further system including an instrument (ultrasonic hand piece), a permeable sleeve and a thermoplastic element, which system, in an assembled state, constitutes a closed load frame in which the thermoplastic element is compressed and axial shortening of the thermoplastic element is compensated by a driver spring. The system further includes means for preventing shock-like action of the driver spring on the system, which means are activated when the system is assembled and before the liquefaction step is started.

Methods for establishing an anchoring in hard tissue or corresponding replacement material or for reinforcing (augmenting) hard tissue with the aid of in situ liquefaction of a material having thermoplastic properties by application of energy, in particular ultrasonic vibration energy, which methods form the basis of the method according to the invention, are disclosed e.g., in the following publications: U.S. Pat. Nos. 7,335,205, 6,921,264, WO2009/010247, WO2009/055952, WO2010/045751, WO0010/127462.

The full disclosure of all the publications cited above is incorporated herein by reference.

SUMMARY OF THE INVENTION

It is the object of the present invention to improve the above briefly described known systems and methods, which serve for establishing an anchorage or a reinforcement in an object with the aid of a material having thermoplastic properties being positioned in a permeable sleeve before or after the permeable sleeve is positioned relative to the object to be liquefied in situ and displaced in a liquefied state to the outside of the permeable sleeve. The system serves in particular for establishing an anchorage in hard tissue or corresponding replacement material or for augmenting hard tissue but may also serve similar purposes in non-medical technology fields. In the medical field, the invention serves in particular for augmenting bone screws, in particular poly-axial pedicle screws. The improvement to be achieved by the invention regards scope, simplicity and ease of handling, and safety of system and method as well as repeatability of high product quality, in particular, for successive use of permeable sleeves and/or thermoplastic elements of differing axial lengths.

The system according to the invention is in principle based on the systems as disclosed in the above cited publications WO2011/054123, WO 2009/010234 and WO2017/054099, i.e. it includes, on the one hand, a transmitting piece arranged in a housing to be axially moveable in the housing in a limited manner and a drive acting on the transmitting piece and urging the latter relative to the hosing in a distal direction, and it includes, on the other hand, a permeable sleeve and a thermoplastic element, wherein, of the transmitting piece, a proximal portion and possibly an energy source coupled thereto is arranged in a proximal housing part, a distal portion extends through a distal housing part, and a distal end is capable of protruding from the distal housing end, wherein, the thermoplastic element is dimensioned to be positionable in the permeable sleeve and the permeable sleeve is adapted to be couplable to the distal end of the housing. Furthermore, the system includes a drive, preferably a driver spring arranged in the proximal housing part, and it is designed to form, in an assembled configuration, a closed load frame as discussed above. The named system is equipped to be adjustable for use with permeable sleeves and/or thermoplastic elements of differing axial lengths, by means which render the effective axial length of the distal housing part adjustable or by furnishing it with a plurality of distal housing parts or transmitting pieces of which a selected one having a suitable axial length is used. This measure does not only guarantee identical functioning of the system on use with permeable sleeves and/or thermoplastic elements of differing axial lengths but also for preventing, for such use, inadvertent, direct contact of the transmitting piece with the permeable sleeve and therewith damage to the system. The distal housing part is separable from the proximal housing part and is equipped for being used for positioning, before the liquefaction step, the permeable sleeve preferably containing the thermoplastic element in the hard tissue or hard tissue replacement material and possibly for pre-anchoring it therein, e.g., by screwing it into the hard tissue.

The system according to the invention may further be equipped for rendering it suitable for revision of an anchorage as achieved with the system, i.e., for re-liquefaction of a rest of the thermoplastic element within the permeable sleeve and parts of the thermoplastic material displaced to the vicinity of the permeable sleeve, and for removing the permeable sleeve from the hard tissue before the liquefied material is re-solidified. For this purpose, the adjustability of the effective axial length of the distal housing part or the plurality of distal housing parts or transmitting pieces is correspondingly extended.

The system according to the invention may further include auxiliary equipment for easing the transmitting piece away from a rest of the thermoplastic element in the permeable sleeve on completion of the anchoring or reinforcing step, i.e., for slightly moving the transmitting piece in a proximal direction relative to the housing.

The method according to the invention comprises, in the same way as similar known methods, a step of pre-anchoring or positioning the permeable sleeve relative to the hard tissue, a step of assembling the system, a step of liquefaction and re-solidification, and a step of system separation, in which a portion of the system is removed from the hard tissue and at least part of the thermoplastic element, in most cases the whole thermoplastic element and the permeable sleeve, remain in the hard tissue. The method according to the invention further includes a step of length adaptation, which step is carried out during assembly of the system, in particular before the transmitting piece is introduced into the permeable sleeve to contact the thermoplastic element positioned therein, and which step includes adjusting the effective axial length of a single distal housing part or selecting from a plurality thereof a distal housing part or transmitting piece having a suitable axial length. Furthermore, the method according to the invention may include a step for easing the transmitting piece away from the rest of the thermoplastic element, this step being carried out after the step of liquefaction and re-solidification and before the step of system separation.

The further method embodiment regarding revision includes a step of assembling the system, a step of liquefaction, and a step of system separation, wherein the steps of liquefaction and of separation are carried out immediately after each other, in particular with very little change of the tooling, preferably with just decoupling of the distal housing part from the proximal housing part and removing the latter together with the transmitting piece. The revision method further includes a step of length adjustment, which step is carried out during assembly of the system, in particular before the transmitting piece is introduced into the permeable sleeve to contact the rest of the thermoplastic element positioned therein, and which step includes adjusting the axial length of a single distal housing part or selecting from a plurality thereof a distal housing part or transmitting piece having a suitable axial length.

The same as for similar, known systems and methods, it is valid also for system and method according to the invention that the material having thermoplastic properties is either bio-resorbable or not bio-resorbable and is e.g., a thermoplastic polymer, copolymer or polymer mixture based e.g., on polylactide. The thermoplastic polymer may contain a filler for reinforcement of the polymer or for other purposes. The material having thermoplastic properties is chosen in view of the anchorage or reinforcement to be established with its help, in particular in view of the load the anchorage or the reinforced tissue is to bear, and it is chosen in view of the energy to be used for its liquefaction. Preferably, the thermoplastic element is fully made of the material having thermoplastic properties but may also include portions of different materials, in particular a proximal portion.

The most preferred embodiment of the system according to the invention includes an ultrasonic handpiece connected to a supply and control unit with the aid of a cable, as well as a cannulated screw (permeable sleeve), in particular a pedicle screw (poly-axial or not poly-axial), to be anchored in hard tissue and a thermoplastic element. The system includes the following: (i) a transducer unit and a sonotrode coupled or couplable to the transducer unit and a driver spring, all being arranged in a proximal housing part, the arrangement of transducer unit and sonotrode being acoustically decoupled from the housing and capable to move axially relative to the housing in a limited manner (sonotrode stroke), movement in the distal direction being driven by the driver spring, (ii) the distal housing part is connected or connectable to the proximal housing part with the aid of a releasable coupling (preferably quick release coupling), which in a coupled configuration is capable of transmitting a tensile and a compressive force, wherein the proximal housing part has a larger cross section than the distal housing part and its distal end tapers to a cross section adapted to the smaller cross section of the distal housing part, (iii) the distal housing part and the cannulated screw are couplable to each other in a manner suitable for transmission of torque and of a tensile and a compressive force, wherein the distal housing part includes two cannulated shafts arranged coaxially within each other and enabling rotation and limited axial displacement relative to each other (before the screw is mounted), wherein one of the shafts (preferably the inner shaft) has a distal end being equipped for transmission of torque and compressive force (e.g., polygon shaped push-on coupling) for pre-anchoring the screw and a proximal end equipped for applying such torque, and wherein the other one of the shafts (preferably the outer one) has a distal end equipped in particular for tensile force transmission (preferably a screwed coupling) from the screw, (iv) the coupling between the distal and the proximal housing part is a telescopic arrangement with a plurality of selectable locking positions each one of them corresponding to one of a plurality of differing effective axial lengths of the distal housing part (incremental or step-wise adjustability), (v) the proximal end of the transducer unit protrudes from the proximal end of the housing and is equipped with e.g., an outer thread for being pulled in a proximal direction relative to the housing against the force of the driver spring by rotating a corresponding nut abutting against the housing, for easing the sonotrode away from the thermoplastic element after the liquefaction and re-solidification step, and (vi) there is a releasable coupling (e.g., cooperating threads) between the transducer unit and the sonotrode and the system includes at least one further, slightly longer sonotrode suitable for the revision method.

Further embodiments of the system according to the invention comprise, alternatively or in addition to the above described most preferred embodiment, the following:

The energy source is not an ultrasonic transducer and is possibly not installed in the housing; the energy source provides an alternative type of energy such as e.g., electromagnetic radiation (laser), electric energy or thermal energy and the thermoplastic element and/or the permeable sleeve are possibly adapted for absorption of the transmitted energy for providing the heat necessary for the liquefaction.

The driver spring is either a compression spring arranged for pushing the transmitting piece away from the proximal end of the housing or it is a tension spring arranged for pulling the transmitting piece away from the proximal end of the housing.

The drive is not a driver spring but an alternative drive suitable for biasing and moving the transmitting piece, such as e.g., a hydraulic, pneumatic or electric drive. Furthermore, the transmitting piece may be manually driven, for which purpose e.g., a corresponding driving lever with an end protruding from the housing is to be provided.

The equipment for adjusting the effective axial length of the distal housing part is not integrated in the coupling between the separable distal and proximal housing parts but is separately provided in the distal housing part or in a distal portion of the proximal housing part.

The permeable sleeve is not a screw to be pre-anchored in the hard tissue or corresponding replacement material by being rotated, but it is e.g., a pin with or without mechanical retention means such as e.g., ribs or barbs, and, therefore, the coupling between distal housing part and permeable sleeve does not need to be equipped for torque transmission.

The distal housing part is not designed as a double but as a single cannulated shaft.

The adjustability of the effective axial length of the distal housing part is not incremental but is continuous, e.g., constituted by a pair of cooperating threads.

The equipment for adjusting the effective axial length of the distal housing part is designed not only for accommodating a set of predefined permeable sleeves and/or thermoplastic elements, but also for corresponding revision procedures.

Instead of a length adjustability of the distal housing part, the system includes a set of distal housing parts, each having a different axial length and each being couplable to the same proximal housing part.

The means for easing separation of the transmitting piece from the thermoplastic element after the liquefaction and re-solidification step does not act on an element coupled to the transmitting piece and protruding from the proximal end of the housing, but is arranged to act through the housing on the transmitting piece or on an element coupled thereto (e.g., lever arranged for being activated from outside of the housing) or on the coupling between the proximal and the distal housing part.

The system is not adjustable for accommodation of permeable sleeve and/or thermoplastic element of differing axial lengths and is possibly not equipped for the revision method, but is solely equipped for easing separation of the transmitting piece from the thermoplastic element.

The method for anchoring or reinforcing according to the invention and using the above detailed most preferred embodiment of the system includes (i) a step of pre-anchoring the cannulated screw in the hard tissue with the aid of the distal housing part being separated from the proximal housing part, wherein the distal housing part is coupled to the screw, and a suitable handle may be coupled to the proximal end of the corresponding one of the shafts of the distal housing part for transmitting torque and compressive force to the screw, a step of introducing the thermoplastic element into the screw, which step is carried out before or after the pre-anchoring step, (ii) a step of assembling the system by coupling the proximal housing part to the distal housing part and simultaneously or beforehand adapting the system to a specific pair of screw and thermoplastic element to be used, (iii) a step of liquefaction and re-solidification, the step being started by activating the driver spring and the transducer unit and liquefaction being ended by a stop limiting the stroke of the transmitting piece and deactivation of the transducer unit, (iv) if applicable, a step of easing separation of the transmitting piece from the thermoplastic element, (v) a step of de-coupling the distal housing part from the cannulated screw, and (v) a step of removing the housing together with the transmitting piece from the now fully anchored and possibly augmented cannulated screw.

Further embodiments of the anchoring and reinforcing method according to the invention, which do not follow in a straight manner from the above listed alternatives and additions to the most preferred system, include the following alternative or additional steps:

The permeable sleeve is, after the liquefaction process, not left in the hard tissue but is removed from the operation site being still coupled to the distal housing part.

The permeable sleeve is not positioned in the hard tissue or hard tissue replacement material but between hard tissue or replacement material and a foreign body, e.g., an implant or graft.

The revision method using the most preferred system as detailed above includes the following steps: (i) a step of adapting the system for the revision method by coupling a transmission piece with an axial length adapted to revision of the anchored screw, (ii) a step of assembling the system, by coupling the distal housing part to the screw being anchored in the hard tissue and coupling the proximal housing part to the distal housing part, (iii) a step of liquefaction by activating the driver spring and the transducer unit, liquefaction being ended when the transmitting piece reaches its above mentioned stop, (iv) a step of system separation including un-coupling the proximal housing part from the distal housing part, and (v) a step of rotating the corresponding shaft of the distal housing part and therewith the screw out of the hard tissue, wherein steps (iv) and (v) are carried out after each other and immediately after step (iii). Some of the above listed additions and alternatives for the system and the anchoring or reinforcing method are, if suitably adapted, also applicable for the revision method.

BRIEF DESCRIPTION OF THE DRAWINGS

Exemplary embodiments of the invention are described in further detail in connection with the appended FIGS., wherein:

FIGS. 3A, 3B, 3C and 3D illustrate the revision method, wherein FIG. 3A shows the system used for establishing the anchoring, FIGS. 3B/C show the system with an adapted transmitting piece suitable for the revision, ready for the liquefaction (FIG. 3B) and on completion thereof (FIG. 3C), and FIG. 3D shows the system with an adapted distal housing part suitable for the revision;

FIG. 4B shows an example of such equipment;

FIGS. 5A, 5B and 5C illustrate a preferred embodiment of the system according to the invention, wherein the system includes a length-adjustable quick release coupling between distal and proximal housing part, and wherein the systems of FIGS. 5A and 5B are adapted to differing permeable sleeves and wherein FIG. 5C shows a detail of the distal housing part on a larger scale;

DETAILED DESCRIPTION OF THE INVENTION

Figure 1A:
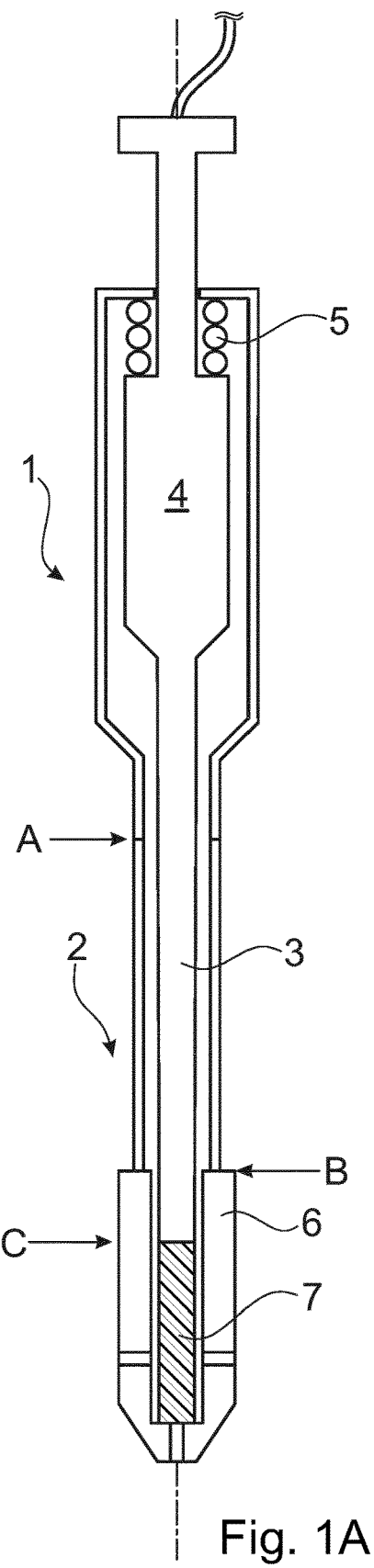
FIGS. 1A and 1B show, in a very schematic manner, a known system for establishing an anchorage or reinforcement in hard tissue with the aid of liquefaction of a material having thermoplastic properties, the system being shown in a configuration ready for the liquefaction step (FIG. 1A) and after the liquefaction step (FIG. 1B)

In all appended FIGS., same reference numerals designate same elements or similar elements serving same functions.

Figure 1B:
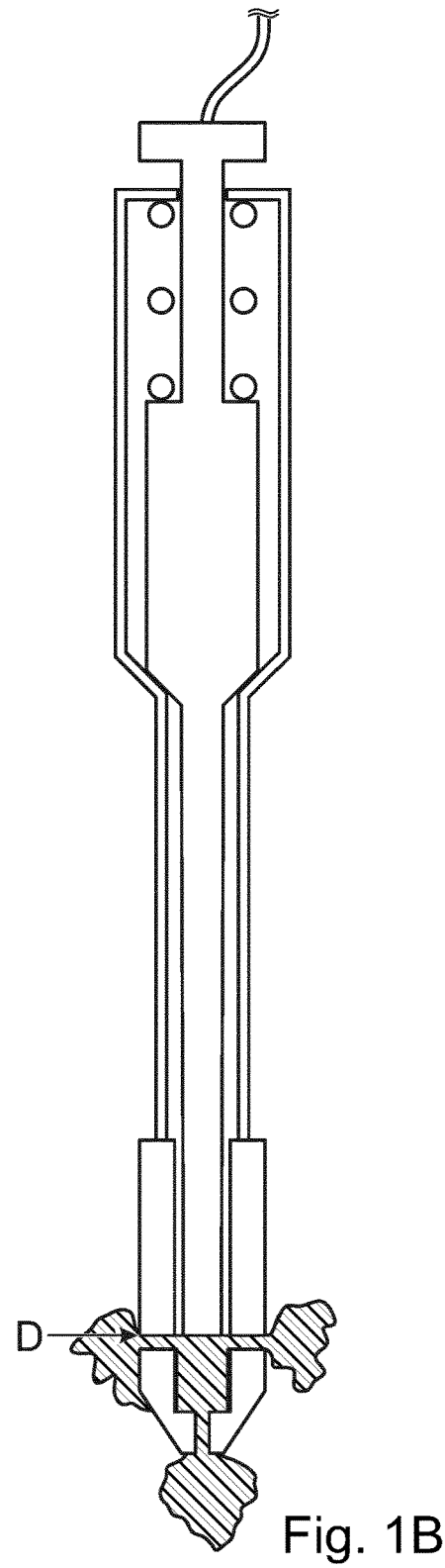

FIGS. 1A and 1B illustrate, in a very schematic manner, the principle of the system according to the state of the art, of which the invention constitutes a further development. The system is shown sectioned along its longitudinal axis and in an assembled configuration. FIG. 1A shows the system ready for the liquefaction step and FIG. 1B on completion of the liquefaction step. The system includes a housing with a proximal housing part 1 and a distal housing part 2, the two housing parts 1 and 2 fixed to each other in a location A or forming an integral unity. In the proximal housing part 1, the proximal end of the transmitting piece 3 and possibly coupled thereto the energy source 4, and the driver spring 5 are arranged in a per se known and therefore not further illustrated manner. A distal portion of the transmitting piece 3 extends through the distal housing part 2 and protrudes from the distal end thereof. For rendering the system particularly suitable for minimally invasive surgery, the distal housing part 2 has preferably a smaller cross section than the proximal housing part 1, wherein the distal end of the proximal housing part 1 tapers down to a reduced cross section adapted to the smaller cross section of the distal housing part 2. The permeable sleeve 6 with the thermoplastic element 7 positioned therein is coupled to the distal end of the distal housing part 2 (location B).

The system parts are dimensioned and arranged such that, in the initial configuration as shown in FIG. 1A, the transmitting piece 3 is in a most proximal position and is preferably locked in this position and the distal face of the transmitting piece 3 has substantially the same axial position C as the proximal face of the thermoplastic element 7. For the liquefaction step, the transmitting piece 3 is unlocked to be pressed against the thermoplastic element 7 by the driver spring 5 and to be moved in distal direction to compensate loss of axial length of the thermoplastic element 7 due to the dislocation of the liquefied material (dislocated material designated 7.1 in FIG. 1B). This movement is limited with the aid of a stop, constituted e.g., by the cross section reduction of the proximal housing part 2, as shown in FIG. 1B. The stop is preferably arranged such that when the transmitting piece 3 reaches the end of its stroke, its distal end is still distanced from the bottom of the central opening of the permeable sleeve 6 (axial position D) such that a rest of the thermoplastic element 7 remains in the permeable sleeve 6 and contact between the transmitting piece 3 and the permeable sleeve 6 is prevented. The stroke of the transmitting piece may be manually shortened by deactivation of the energy source or the system may be equipped with an axially displaceable stop for presetting a desired length of the stroke of the transmitting piece.

Figures 2A, 2B, 2C:
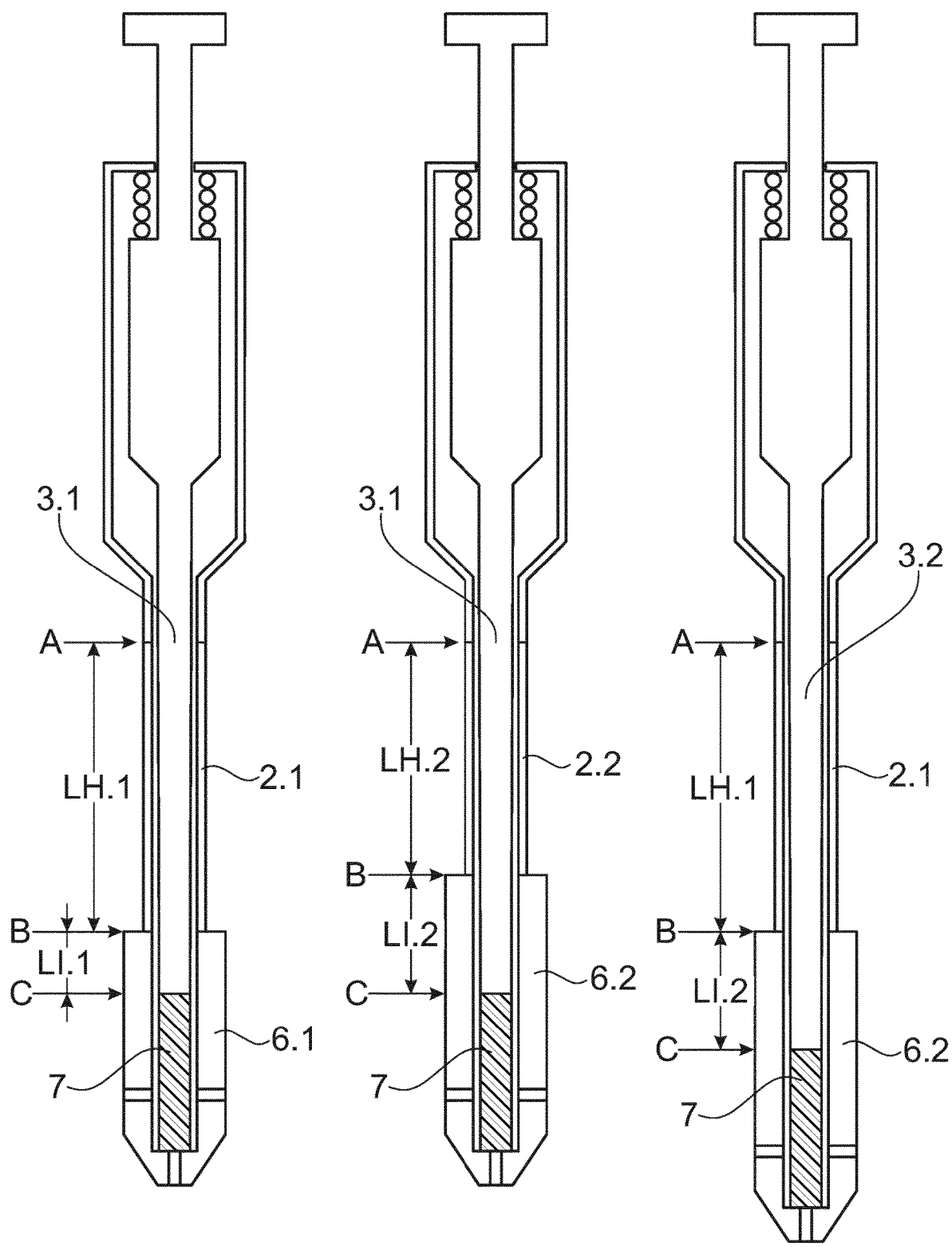
FIGS. 2A, 2B, and 2C illustrate the adjustment of the system according to the invention: with a first permeable sleeve and corresponding distal housing part and transmitting piece (FIG. 2A), with a second permeable sleeve and adapted distal housing part (FIG. 2B), and with a second permeable sleeve and adapted transmitting piece (FIG. 2C)

FIGS. 2A-2C illustrate the principle of the system according to the invention which is equipped for accommodating permeable sleeves and/or thermoplastic elements of differing axial lengths without change to its functioning. As in FIGS. 1A-1B, the system is shown axially sectioned and in an initial configuration, i.e. ready for the liquefaction step. FIG. 2A shows the assembled system, wherein the permeable sleeve 6.1 has a first effective axial length, the distal housing part 2 has an effective axial length LH.1 (distance between axial positions A and B), the thermoplastic element 7 has an axial length such that the distal end of the transmitting piece 3.1 has to reach into the permeable sleeve 6.1 by a depth LI.1 (distance between axial positions B and C) for being in contact with the thermoplastic element 7. FIGS. 2B and 2C show the system with a permeable sleeve 6.2 having a second, greater axial length and with a same thermoplastic element 7. This results in a greater depth LI.2, which is compensated by a correspondingly adapted smaller axial length LH.2 of the distal housing part 2 (FIG. 2B) or by a correspondingly longer transmitting piece 3.2 (FIG. 2C). Generally speaking, the axial length of the distal housing part 2 or of the transmitting piece 3 is adapted to the depth LI (distance between axial positions B and C) by which the transmitting piece 3 needs to initially reach into the permeable sleeve 6 to contact the proximal face of the thermoplastic element 7.

FIGS. 2A-2C show clearly, that the illustrated system adjustment to differing axial lengths of permeable sleeve 6 and/or thermoplastic element 7 does in no way interfere with the arrangement of proximal housing part 1, transmitting piece 3 and driver spring 5 and therefore does not interfere with the functioning of the system.

The inventive system adjustment as illustrated by FIGS. 2A-2C is realized by a corresponding adjustment of the effective distal length of the distal housing part 2 or by providing a plurality of distal housing parts 2 or transmitting pieces 3 of differing axial lengths and by mounting a selected one of the plurality in the system. If the system works with vibrational energy and the transmitting piece is designed to vibrate with maximum amplitude at its distal end, adaptation of the axial length of the distal housing part is preferred in particular for larger differences to be compensated, because only small such compensations can be realized with transmitting pieces with only differing axial length, i.e., without adaptation of their vibration characteristics also.

FIGS. 3A-3D illustrate the method of revision using the system as already described in connection with FIGS. 1A-B and 2A-2C. FIG. 3A shows the system on completion of the liquefaction step being part of the anchoring or reinforcing procedure in which the anchorage to be revised is produced. FIG. 3A shows the system according to FIG. 2A in a configuration as illustrated in FIG. 1B, i.e., the transmitting piece 3.1 has reached the end of its stroke and is stopped with its distal end at axial position D, a rest 7.2 of the thermoplastic element 7 remaining in the permeable sleeve 6.1. FIG. 3B shows the assembled system ready for the liquefaction step of the revision method, for which only a small stroke (revision stroke) of the transmitting piece, e.g., of 2 mm, is needed. For enabling this small stroke, the system comprises, compared with the system according to FIG. 3A, a slightly longer (e.g., longer by 2 mm) transmitting piece 3.3 enabling the small stroke necessary for the revision, without the transmitting piece 3.3 to be brought into its initial position. FIG. 3C shows the system after the liquefaction step, in which again the transmitting piece 3.3 is stopped in its final position and its distal end has reached axial position D.1 preferably still being distanced from the bottom of the central opening of the permeable sleeve.

FIG. 3D illustrates the fact that the same as is achievable with the slightly longer transmission piece 3.3 as illustrated in FIGS. 3B-3C can be achieved with a slightly shorter distal housing part 2.3. This means that for being applicable for the revision method, the system is equipped with the same adjustability (adaptable axial length of distal housing part or plurality of distal housing parts or transmitting pieces of differing axial lengths) as above described for its adjustability for permeable sleeves and or thermoplastic elements, wherein because of the small size of the stroke of the transmitting piece necessary for the revision, the embodiment with the plurality of transmitting pieces may be preferred. If a revision specific distal housing part with a slightly shortened axial length is provided and if the permeable sleeve is a cannulated screw, it is advantageous to equip the proximal end of this distal housing part with means for applying torque to the screw for removing it from the hard tissue, e.g., with a gnarled grip or a hand wheel (not shown).

Figure 4A:
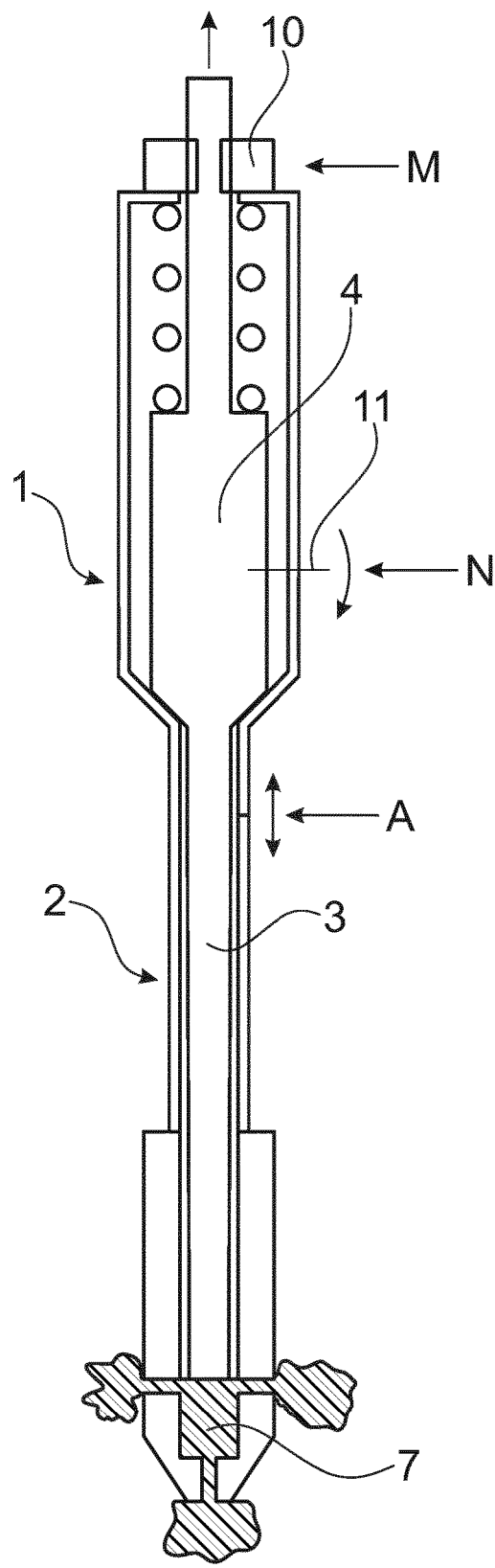
FIGS. 4A and 4B illustrate the step of easing the transmitting piece away from the thermoplastic element before system separation, FIG. 4A illustrating very schematically equipment for such easing

FIG. 4A shows again in a very schematic manner, the system according to FIG. 2A which is shown in a configuration as illustrated in FIG. 1B (after the liquefaction step of the anchoring or reinforcing procedure) and which is further equipped for easing separation of the transmitting piece 3 from the thermoplastic element 7 before system separation on completion of the liquefaction and re-solidification step. Such easing is in particular necessary in cases in which the material of the thermoplastic element 7 is liquefied not only in a distal part of the element 7 but also in the vicinity of the proximal face thereof and, after re-solidification, tends to stick to the distal face of the transmitting piece 3. For easing the transmitting piece 3 away from the thermoplastic element 7, the transmitting piece is forced relative to the housing and against the force of the driver spring 5 in a proximal direction. For this purpose, forcing means are provided in either one of axial positions M, N or A. A suitable such forcing means in axial position M is e.g., a threaded nut 10 cooperating with a thread on a portion of the transmitting piece 3 or of the transducer unit 4 respectively, which nut 10 abuts against the proximal end of the housing and, on rotation, forces the transmitting piece 3 in a proximal direction relative to the housing and therewith away from the thermoplastic element 7. A suitable forcing means in an axial position N is e.g., a pivoting lever 11 acting on the transmitting piece 3 or on the transducer unit 4 respectively and reaching through an opening in the proximal housing part 1. Pushing the lever end protruding from the housing in a distal direction relative to the housing forces the transmitting piece 3 proximally. A suitable forcing means for position A acts to slightly increase the axial length of the housing, preferably by forcing the proximal housing part 1 away from the distal housing part 2, which again forces the transmitting piece 3 away from the thermoplastic element 7. Such forcing means is e.g., a pair of corresponding threads one arranged on the proximal and the other one arranged on the distal housing part.

Figure 4B:
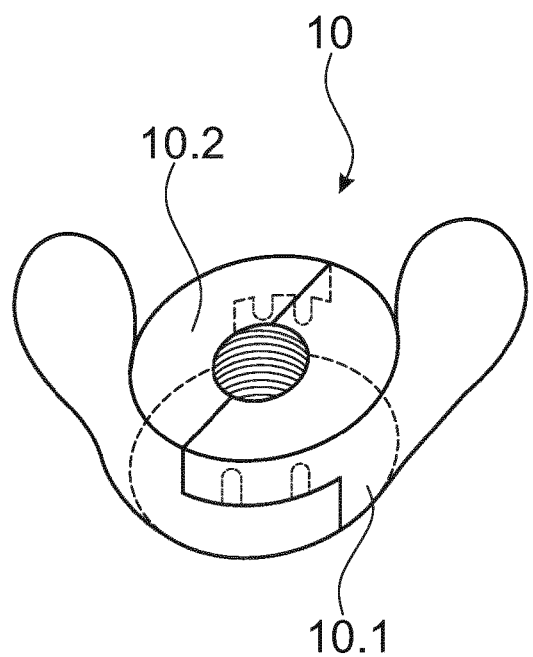

FIG. 4B illustrates in more detail an exemplary easing means being applicable to be used in axial position M as already mentioned above. The easing means is a nut 10, preferably a wing nut with an interior thread being adapted to a cooperating thread provided on the proximal end of the transmitting piece or transducer unit respectively. For being easily mounted around this proximal end, in particular if a cable is connected thereto, the nut 10 may include separable left and right parts 10.1 and 10.2, which include cooperating pairs 10.3 of peg and opening. The two nut parts are positioned around the cable or the proximal part of transmitting piece or transducer unit while being axially distanced from each other and aligned to each other. Then, they are moved axially towards each other such that each peg is introduced into the corresponding opening and therewith the two nut parts are secured relative to each other in radial direction, rendering the nut ready for operation. In the same way applicable as the wing nut according to FIG. 4B are e.g., a two-part hand wheel with an inner thread, a gripper with gripping jaws equipped with a thread on their gripping surfaces, or a pivoting lever.

Figure 5A:
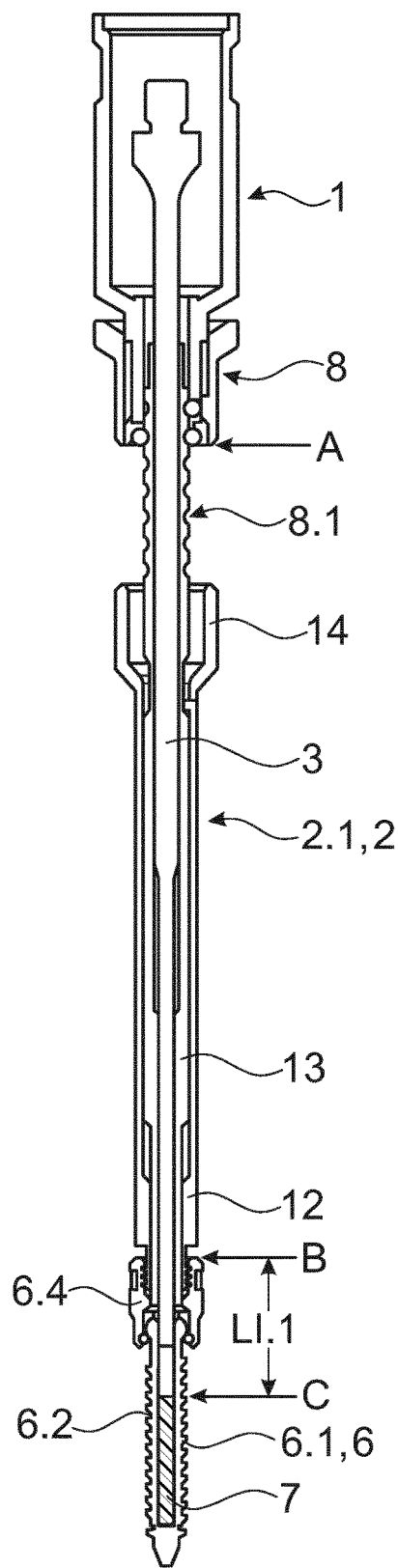
Figure 5B:
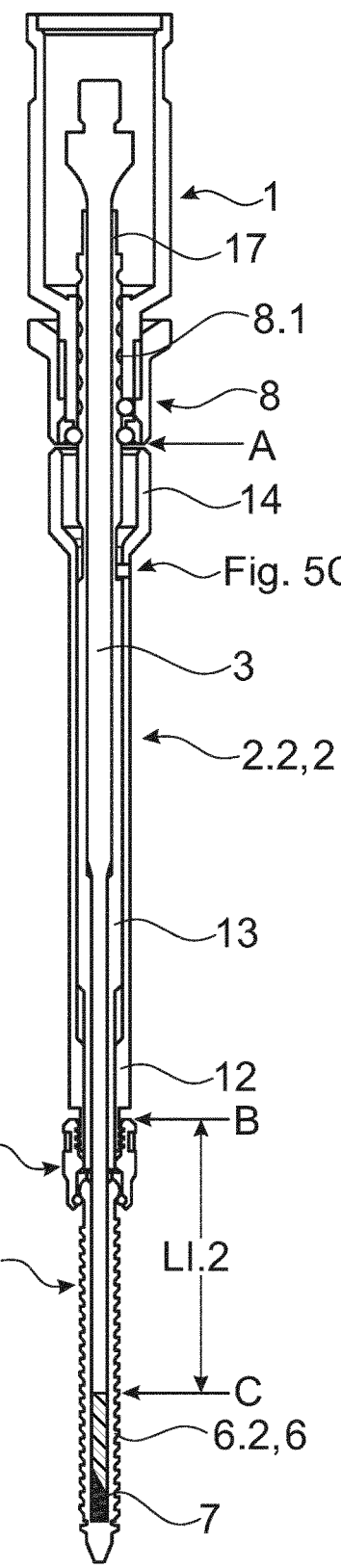
Figure 5C:
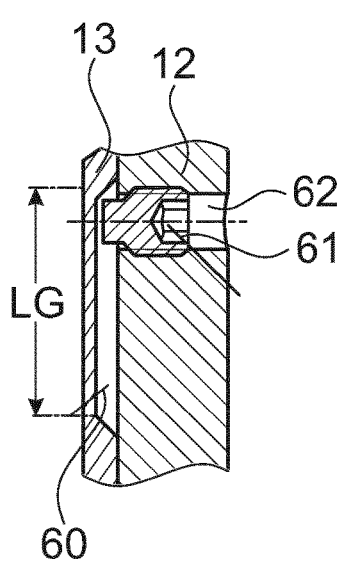
Figure 6:
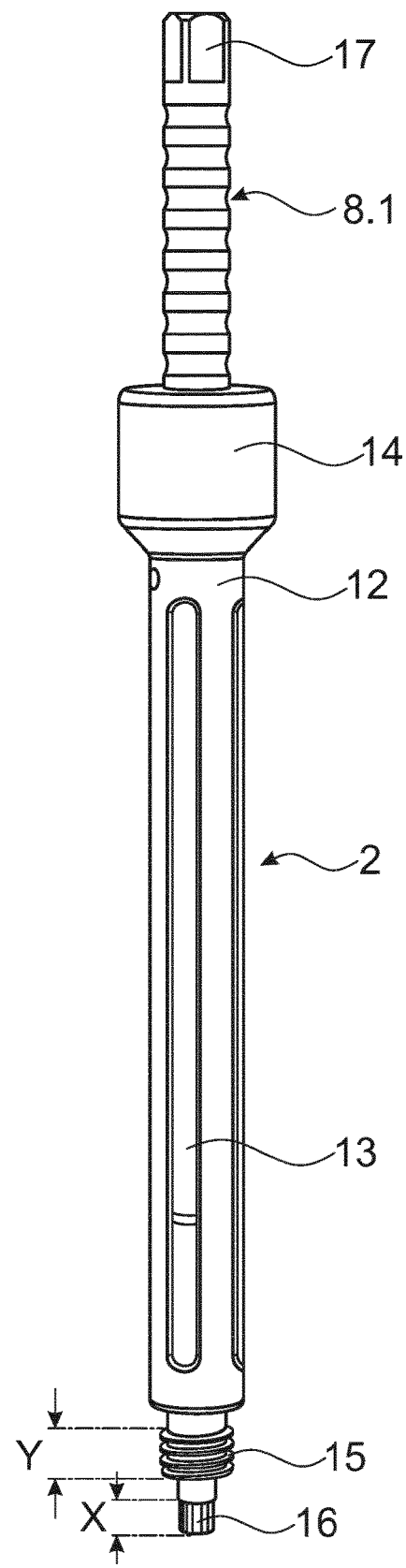
FIG. 6 is a lateral view of the distal housing part of the system according to FIGS. 5A and 5B.

FIGS. 5A-5C and FIG. 6 show in more detail a first exemplary embodiment of the system according to the invention, which is the most preferred embodiment whose features have already been listed further above. FIGS. 5A-5B show the system in section along the longitudinal axis and in a configuration ready for the liquefaction step of the anchoring or reinforcing procedure. FIG. 5C shows on a larger scale a detail of the distal housing part and FIG. 6 is a lateral view of the distal housing part without a permeable sleeve, or poly-axial pedicle screw respectively, coupled thereto.

As best illustrated by FIGS. 5A-5B, the system includes system parts as described in connection with FIGS. 1A-3D, wherein the proximal housing part is shown only partially and the transducer unit and driver spring are not shown. FIGS. 5A and 5B differ from each other like FIGS. 2A and 2B by including permeable sleeves 6.1 and 6.2 of differing axial lengths, the differing depths LI.1 and LI.2 (distance between axial positions B and C) being compensated by adaptation of the effective axial length of the distal housing part 2 (distance between axial positions A and B). The distal housing part 2 is releasably coupled to the proximal housing part 1 with the aid of a quick release coupling 8 and the adjustability is integrated in this coupling 8, i.e., the coupling is a releasable telescopic coupling arrangement with a plurality of axial locking positions, wherein locking of the coupling in a selected one of the locking positions results in a selected effective axial length of the distal housing part 2

(distance between positions A and B). The coupling 8 and its function is described in detail further below in connection with FIG. 7.

As best illustrated by FIG. 6, the distal end of the distal housing part 2 is equipped for being coupled to the proximal end of the permeable sleeve 6, which in the illustrated system is a cannulated poly-axial pedicle screw 6.3 with a rod receiver piece 6.4 held freely rotatable and pivoting by the screw head and including an inner thread for eventually receiving a locking piece for locking a rod in the receiver piece 6.4. The distal housing part 2 is a double cannulated shaft, wherein the outer shaft 12 is rotatable and movable in an axial direction in a limited manner relative to the inner shaft 13 and includes a proximal gripping portion 14 and a distal outer thread 15 dimensioned for being coupled to the inner thread of the receiver piece 6.4. The inner shaft 13 includes a proximal portion suitable as male part 8.1 of the coupling 8. Furthermore, the inner shaft 13 is equipped like a screw driver, i.e. its distal end 16 is shaped to cooperate with the screw head for transmitting torque and a compressive force to the screw, e.g., has a polygon cross section to cooperate with a corresponding polygon opening in the screw head (push-on coupling), and its proximal end 17 is equipped for coupling e.g., a handle (nor shown) thereto, e.g., by having again a polygon cross section cooperating with a polygon-shaped opening in the handle.

FIG. 5C shows on a larger scale the connection of the inner and outer shafts 13 and 12 constituting the distal housing part 2 of the system according to FIGS. 5A-5B and 6. For the two shafts being rotatable and axially moveable relative to each other, the inner shaft 13 includes a circumferential groove 60 of an axial extension LG and the outer shaft 12 includes a locking element 61 extending into the groove 60, the locking element 61 being mounted in a through bore 62, when the inner shaft 13 is positioned in the outer shaft 12.

For coupling the poly-axial pedicle screw including the screw 6.3 and the receiver piece 6.4 to the distal housing part 2 as illustrated in FIGS. 5A/B and 6, the distal end 16 of the inner shaft 13 is pushed into the corresponding opening in the head of screw 6.3, and then the receiver piece 6.4 is positioned coaxially with the screw 6.3 and the distal housing part and the outer shaft 12 is rotated for engaging the distal thread 15 of the outer shaft 13 with the inner thread of the rod receiver piece 6.4, whereby the locking piece 61 moves in a distal direction in the groove 60. Therein the axial extension LG of groove 60 is adapted to the axial lengths of the distal ends 15 and 16 of the two shafts 12 and 13 such that LG is larger than the axial length x of the polygon end 16 of the inner shaft 13, or the depth to which this end can be introduced into the screw head respectively, and shorter than the sum of x plus the axial lengthy of the thread 15 of the outer shaft 12. This means that by threading the thread 15 into the receiver piece 6.4, the two shafts 12 and 13, the screw 6.3 and the receiver piece 6.4 can be axially tensioned together when the locking piece 61 has reached its most distal position in the groove 60, such that the assembly of poly-axial screw and double-shaft distal housing part 2 form a rigid entity in which the screw head is forced into the receiver piece and therewith is oriented as coaxially as possible with the distal housing part.

Alternative designs of the distal housing part 2 and in particular of the distal end thereof are dependent on the proximal end of the permeable sleeve 6 to be used in the system. For cooperation with a threaded permeable sleeve (screw) including a proximal end (e.g., screw head) with a threaded opening and an outer non-circular (e.g., hexagonal) shape, the distal housing part 2 may again include an inner and an outer cannulated shaft, wherein the function of the two shafts is, compared to the distal housing part as shown in FIGS. 5A-5B and 6, is reversed as described for the applicator in the above cited publication WO 2011/091545. Designing couplings between any permeable sleeve suitable for the system according to the invention and a corresponding distal housing part constitutes no problem for one skilled in the art, wherein, as detailed further above, the coupling needs to be capable of transmitting the tensile load acting on it during the liquefaction process and any compressive force necessary for positioning and possibly pre-anchoring the permeable sleeve in the hard tissue before the step of liquefaction and re-solidification, and wherein the coupling needs to be releasable when the permeable sleeve is finally positioned and anchored in the tissue, i.e., with as little force acting on the permeable sleeve as possible, and, in particular in the case of application in minimally invasive surgery, with the necessary handling restricted to the proximal end of the distal housing part 2.

Figure 7:
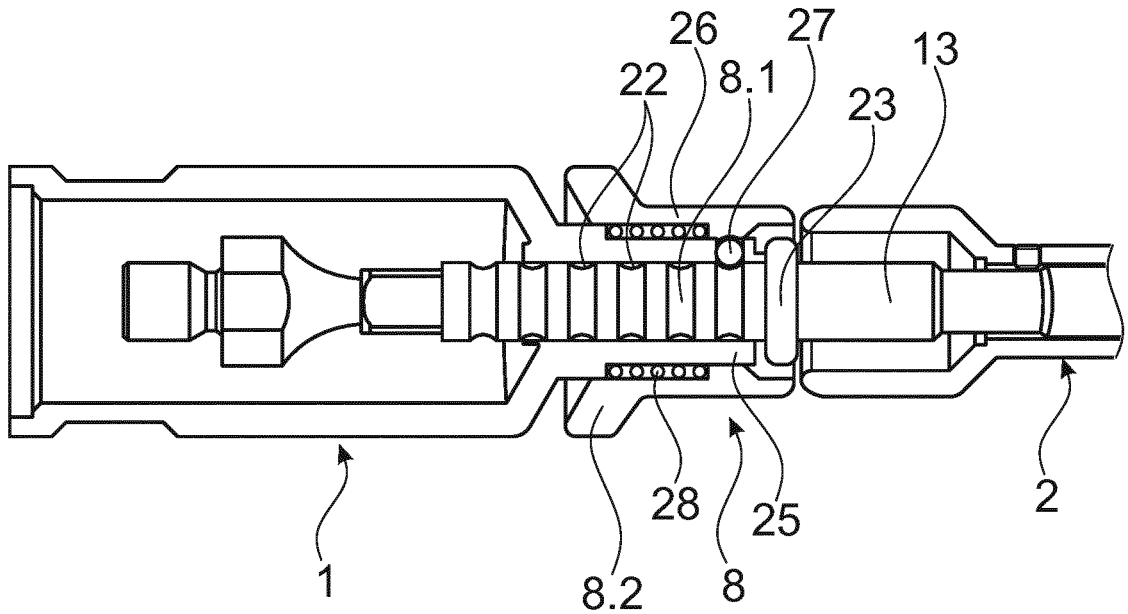
FIG. 7 shows on a larger scale the length adjustable quick release coupling between distal and proximal housing part of the system as shown in FIGS. 5A and 5B.

FIG. 7 illustrates in further detail the functioning of the coupling 8 between the distal housing part 1 and the proximal housing part 2 as already shown in FIGS. 5A-5B, wherein this coupling is shown in section along the longitudinal axis. The coupling 8 is a quick release coupling with integrated telescopic length adaptability. FIG. 7 shows the coupling configuration in which the effective axial length of the distal housing part 2 is the smallest possible. The male part 8.1 of the coupling 8 is constituted by the proximal end of the inner shaft 13 of the distal housing part 2 and includes a plurality of circumferential grooves 22 and a resilient setting ring 23. The setting ring 23 is dimensioned for firmly sitting in a selected one of the grooves 22, for being able to be manually moved from one of the grooves 22 to another one, and for not being able to enter the distal opening of the female coupling part 8.2. This female coupling part 8.2 is constituted by the distal end of the proximal housing part 1, which, for this function, in a per se known manner, has an inner cross section adapted to the outer cross section of the male part 8.1 and is equipped with a spring loaded locking ring 26 and at least one locking ball 27 positioned in an opening in the proximal housing part 1, wherein the locking ball 27 is held in the opening by the locking ring 25 in its locking position and is protruding into the inside of the proximal housing part 1. Movement of the locking ball 27 radially outward and therewith allowing the male coupling part 8.1 to be introduced into and axially moved in the female coupling part 8.2 is possible only, when the locking ring 25 is moved axially against the action of its spring 28.

For coupling the distal housing part 2 to the proximal housing part 1 and at the same time setting the effective axial length of the distal housing part 2, the setting ring 23 is positioned in the corresponding groove 22, then, the locking ring 26 is moved against the action of its spring 28 from its locking position to its inactive position and the male coupling part 8.1 is introduced into the female coupling part 8.2 as deep as the setting ring 23 allows. Then the locking ring 26 is released to resume, driven by its spring 28, its locking position.

Figure 8:
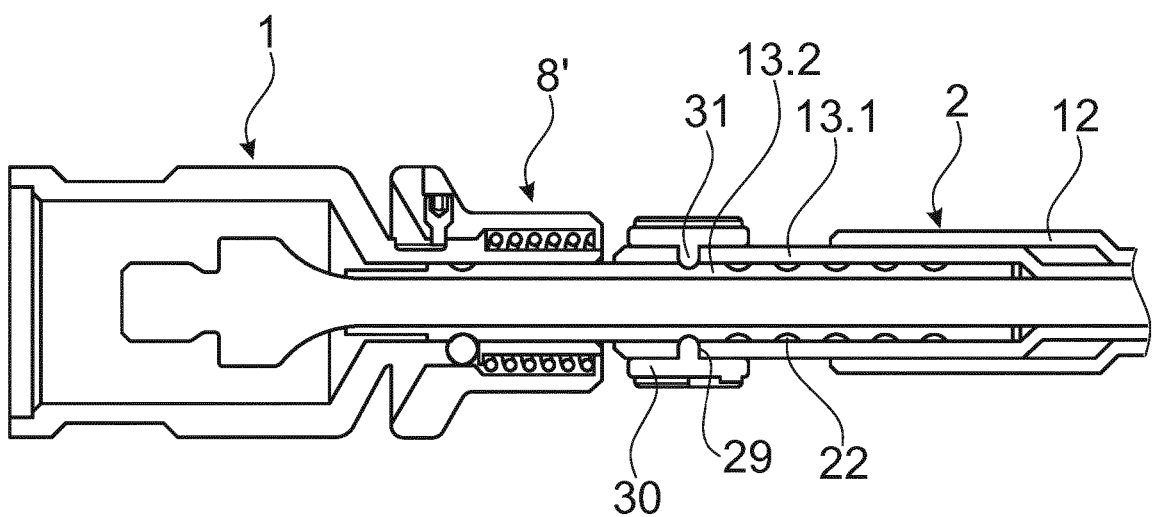
FIG. 8 shows a further example of a length adjustment suitable for a distal housing part.

FIG. 8 shows in the same manner as FIG. 7 an alternative embodiment of a telescopic length adjustment arrangement, which, in this case, is not releasable and is therefore applicable in a system comprising, in addition to the telescopic length adjustment arrangement, a releasable coupling 8' between proximal and distal housing parts, which releasable coupling 8' has one locking position only. The non-releasable telescopic length adjustment arrangement connects two portions of the distal housing part or in the illustrated case two portions 13.1. and 13.2 of the inner shaft 13, wherein the two portions are designed for telescopically fitting inside each other, wherein the male portion 13.2 includes a plurality of axially spaced grooves 22 and the female portion 13.1 a through bore 29, and wherein a resilient locking clip 30 is provided, the locking clip 30 including an inner projection 31 adapted to be able to reach through the through bore 29 into a selected one of the grooves 22 which is aligned with the through bore 29, and therewith locking the male and the female portions 13.2 and 13.1 relative to each other in one of a plurality of possible locking positions. Therein, suitable provisions are preferably provided for preventing complete separation of the female and male portions.

Figure 9:
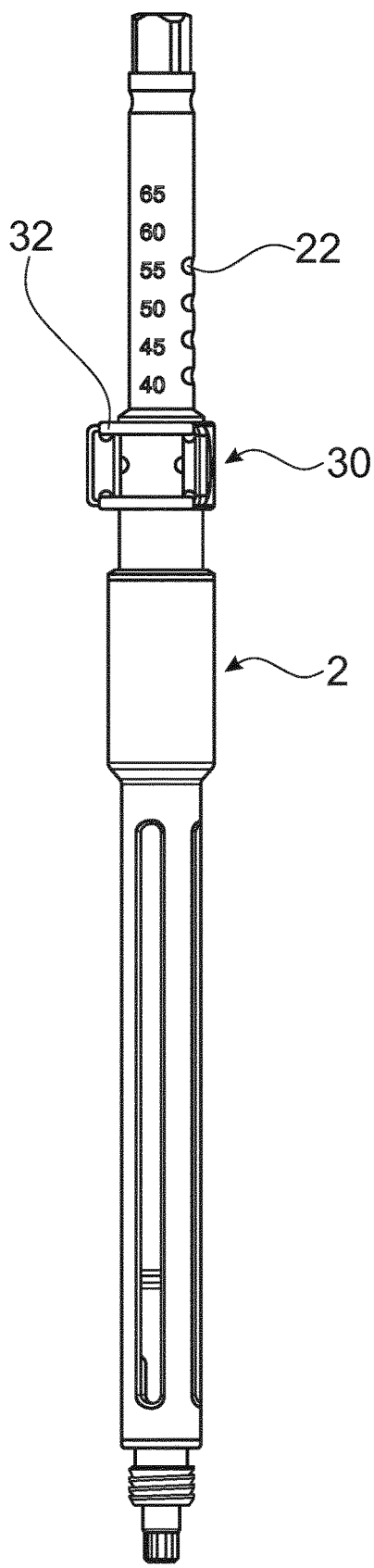
FIG. 9 is a lateral view of a distal housing part equipped as shown in FIG. 8.

FIG. 9 shows, in its entirety and separated from other system parts, the distal housing part 2 of the system embodiment which is partially shown in FIG. 8 and it shows in particular the above described resilient locking clip 30 of the telescopic length adjustment arrangement as discussed in connection with FIG. 8. This resilient locking clip 30 is shown in its locking position. For un-locking the telescopic length adjustment arrangement, the resilient locking clip 30 is moved radially away from the distal housing part 2 into a non-locking position in which the protrusion 31 (not visible in FIG. 9) is retrieved at least from the groove 22 to allow relative axial movement between the male and female portions 13.2 and 13.1 and is prevented from falling off the distal housing part 2 e.g., by a resilient safety strap 32.

Figure 10A:
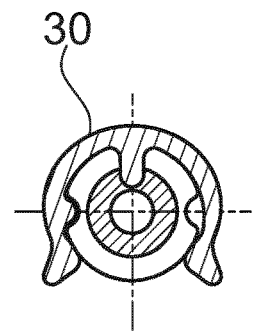
FIGS. 10A and 10B are cross sections through a further example of a length adjustable distal housing part in a locked configuration (FIG. 10A) and in an un-locked configuration (FIG. 10B)
Figure 10B:
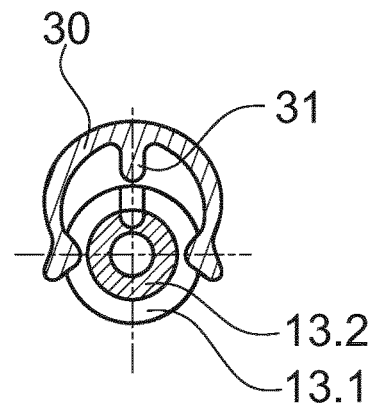

FIGS. 10A-10B are cross sections through a telescopic length adjustment arrangement similar to the one discussed above in connection with FIGS. 8 and 9, wherein FIG. 10A shows the resilient locking clip 30 in its locking position and FIG. 10B in its non-locking position.

Figure 11:
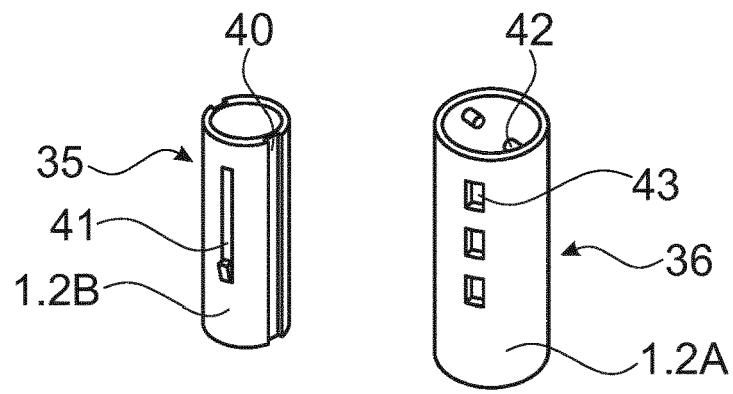
FIGS. 11 and 12 shown, in a schematic manner, further exemplary embodiments of telescopic incremental length adjustment arrangements being suitable for the system according to the invention.
Figure 12:
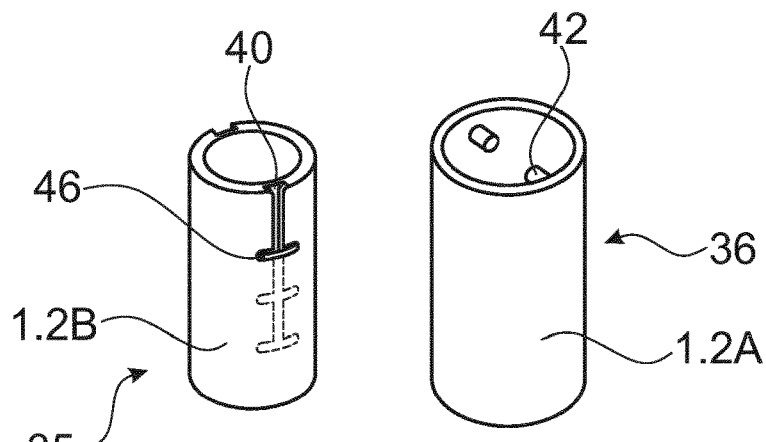

FIGS. 11 and 12 illustrate further exemplary telescopic length adjustment arrangements which may be designed to be releasable (applicable in a system similar to the system according to FIGS. 5A-5B, 6 and 7) or non-releasable (applicable in a system similar to the system according to FIGS. 8 and 9).

According to FIG. 11 the male or inner portion 35 of the arrangement includes at least one longitudinal groove 40 on its outer surface and a resilient wing 41 with one end fixed to the outer surface of the inner portion and an outwardly biased free end, the resilient wing 41 being forcible into a corresponding depression in the named outer surface. The female or outer portion 36 includes at least one protrusion 42 on its inner surface and a plurality of through openings 43. Therein, the groove 40 and the protrusion 42 are adapted to each other for preventing rotation of the inner portion 35 relative to the outer portion 36 and the resilient wing 41 is adapted to the through openings 43 for its free end to be positioned in one of the through openings 43 when the two are aligned to each other such locking the two portions 35 and 36 relative to each other in a selected one of a plurality of locking positions. For unlocking, the free end of the resilient wing 41 is manually pressed to the inside of the through opening 43.

According to FIG. 12, the male or inner portion 35 includes, on its outer surface, at least one longitudinal groove 40 and a plurality of axially distanced cross grooves 46 that cross the longitudinal groove 40 and have closed ends. The outer part 36 includes at least one inner protrusion 42 adapted to be moveable in the longitudinal groove 40 and in the cross grooves 46. For adjusting the axial length of the arrangement according to FIG. 12, the inner protrusion 42 being positioned in one of the cross grooves 46 is aligned with the longitudinal groove 40 by rotating the two portions 35 and 36 relative to each other such allowing relative axial movement between the two portions. For locking the arrangement, the inner protrusion 42 is aligned with a crossing of longitudinal and cross groove and the outer portion 36 is rotated relative to the inner portion 35 to move the protrusion 42 into the cross groove 46 therewith locking the arrangement.

Figure 13:
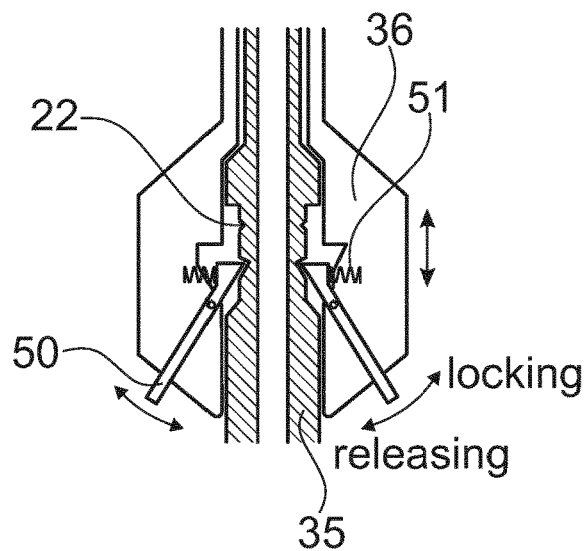
FIG. 13 shows a further exemplary embodiment of a length adjustable quick-release coupling suitable for application in a system according to the invention.

FIG. 13 illustrates a further exemplary embodiment of a telescopic length arrangement. The inner or male portion 35 includes again a plurality of axially spaced circumferential grooves 22 which cooperate with a pair of spring loaded pivoting levers 50 having a locking end situated inside the outer portion 36 and adapted to reach into a selected one of the circumferential grooves 22, and a handle end situated outside of the outer portion 36 to be handleable by an operator. The springs 51 bias the locking ends of levers 50 towards the inner portion 35 for locking the arrangement. For un-locking the arrangement, the handle ends of the locking levers 50 are moved radially inwards to move the locking ends out of the circumferential groove 22 such allowing relative axial movement between the inner and outer portion.

In the preceding FIGS. 5A-13 a selection of exemplary telescopic length adjustment arrangements suitable for the systems according to the invention are described. Therein, all the described arrangements can be designed to be releasable, i.e., allowing complete removal of the male portion from the female portion, or non-releasable, i.e., equipped with suitable stops preventing removal of the male portion out of the female portion. There are a number of further, from other applications well known embodiments of such arrangements which one skilled in the art can adapt without difficulty to the present application.

What is claimed is:

1. A system for establishing an anchorage or a reinforcement in an object with the aid of a material having thermoplastic properties, which is brought to the site of the anchorage or reinforcement in a solid state, is liquefied in situ, and, in a liquefied state, is displaced to contact the object, the system comprising:

a housing with a proximal housing part and a distal housing part, the distal housing part having a smaller cross section than the proximal housing part, a distal end of the proximal housing part tapering down to a cross section similar to the cross section of the distal housing part, and the distal housing part being releasably couplable to the proximal housing part, a transmitting piece suitable for transmitting energy coupled into the transmitting piece from an energy source, the transmitting piece having a proximal and a distal end, the proximal end being arranged in the proximal housing part to be axially moveable in a limited manner and the distal end suitable for extending through the distal housing part and for protruding from a distal end of the distal housing part, a drive being arranged to act between the proximal housing part and the proximal end of the transmitting piece to bias the proximal end of the transmitting piece away from a proximal end of the housing, a permeable sleeve couplable to the distal end of the distal housing part, and a thermoplastic element comprising the material having thermoplastic properties and being positionable in the permeable sleeve, wherein, in an assembled configuration of the system the permeable sleeve with the thermoplastic element positioned therein is coupled to the distal end of the housing, the coupling being designed for tensile load transmission, and the proximal and the distal housing parts, the transmitting piece, the drive, the permeable sleeve and the thermoplastic element form a closed load frame in which the thermoplastic element is compressed between the transmitting piece and the permeable sleeve, and wherein, for enabling use of permeable sleeves and/or thermoplastic elements or for use in a revision method, the system is equipped for adjustment of an effective axial length of the distal housing part or comprises a plurality of distal housing parts or a plurality of transmitting pieces of differing axial lengths.

2. The system according to claim 1, wherein the permeable sleeve is a cannulated screw, and wherein the distal housing part, when separated from the proximal housing part, is equipped for transmitting torque to the screw.

3. The system according to claim 2, wherein the distal housing part comprises an outer cannulated shaft and an inner cannulated shaft being arranged within the outer cannulated shaft, the two shafts being rotatable relative to each other, wherein one of the cannulated shafts is equipped for being coupled to the screw in a manner suitable for transmitting a tensile load, and an other one of the two shafts is equipped for being coupled to the screw in a manner suitable for transmitting torque.

4. The system according to claim 3, wherein the inner cannulated shaft comprises a distal end suitable for transmitting torque and a proximal end suitable for coupling to the proximal housing part and suitable for coupling to a handle for applying torque, wherein the outer cannulated shaft comprises a distal end equipped with a thread dimensioned to cooperate with a thread arranged on a proximal end of the screw and a proximal end suitable for manual rotation of the outer shaft relative to the inner shaft and wherein, when the screw is not coupled to the distal housing part, the inner and the outer shafts are axially moveable relative to each other in a limited manner.

5. The system according to claim 4, wherein the cannulated screw is a poly-axial pedicle screw with a rod receiver piece, wherein the thread comprised by the outer cannulated shaft is dimensioned to cooperate with a thread arranged on the rod receiver piece, and wherein the relative axial movability of the two cannulated shafts is dimensioned for the arrangement of the poly-axial pedicle screw and the two cannulated shafts to be axially tensioned when the two threads are threaded into each other.

6. The system according to claim 1, wherein the energy source is an ultrasonic transducer unit arranged in the proximal housing part, and the transmitting piece is a sonotrode coupled to the transducer unit.

7. The system according to claim 1, wherein the axial length of the distal housing part is incrementally adjustable.

8. The system according to claim 7, wherein adjustability of the effective axial length of the distal housing part is realized by providing a telescopic length adjustment arrangement which is lockable in a selected one of a plurality of axially distanced locking positions, the telescopic length adjustment arrangement comprising a female portion and a male portion, wherein the male portion is axially moveable in the female portion.

9. The system according to claim 8, wherein, the telescopic length adjustment arrangement is integrated in a quick release coupling provided for releasably coupling the distal housing part to the proximal housing part.

10. The system according to claim 9, wherein a depth of introduction of the male portion into the female portion and therewith one of the plurality of locking positions is presettable by positioning a setting ring dimensioned for not being able to enter the female portion in a selected one of a plurality of setting positions.

11. The system according to claim 10, wherein the setting ring is resilient and the setting positions are circumferential grooves provided on the male portion.

12. The system according to claim 8, wherein, for locking the male part in the female part in a selected one of the axial locking positions, a locking ring with a protrusion reaching through the female portion into a selected one of a corresponding opening in the male portion is provided.

13. The system according to claim 1 and further comprising a nut or a gripper with an inner thread adapted to an outer thread provided on a portion of the transmitting piece or the energy source protruding from the proximal end of the proximal housing part.

14. The system according to claim 13, wherein the nut comprises a left and a right part, the two parts comprising cooperating pairs of pegs and openings.

* * * * *